United States Patent
Gupta et al.

(10) Patent No.: US 9,198,614 B2
(45) Date of Patent: Dec. 1, 2015

(54) METHOD AND SYSTEM FOR CHARACTERIZING CHAMBER SPECIFIC FUNCTION

(71) Applicant: PACESETTER, INC., Sylmar, CA (US)

(72) Inventors: Kritika Gupta, San Francisco, CA (US); Rupinder Bharmi, Canyon Country, CA (US); Bruce A. Morley, Garland, TX (US); Laurence S. Sloman, West Hollywood, CA (US); Wenbo Hou, Santa Clara, CA (US); Xiaoyi Min, Camarillo, CA (US); Riddhi Shah, San Jose, CA (US); Edward Karst, Los Angeles, CA (US); Gene A. Bornzin, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 93 days.

(21) Appl. No.: 14/024,459

(22) Filed: Sep. 11, 2013

(65) Prior Publication Data

US 2015/0073287 A1   Mar. 12, 2015

(51) Int. Cl.
| | |
|---|---|
| *A61B 5/053* | (2006.01) |
| *A61B 5/06* | (2006.01) |
| *A61B 5/00* | (2006.01) |
| *A61N 1/365* | (2006.01) |
| *A61B 5/02* | (2006.01) |
| *A61B 5/0452* | (2006.01) |
| *A61N 1/368* | (2006.01) |

(52) U.S. Cl.
CPC ............ *A61B 5/4836* (2013.01); *A61B 5/02028* (2013.01); *A61B 5/0452* (2013.01); *A61B 5/0538* (2013.01); *A61N 1/36521* (2013.01); *A61N 1/36585* (2013.01); *A61B 5/686* (2013.01); *A61N 1/365* (2013.01); *A61N 1/3682* (2013.01); *A61N 1/3684* (2013.01)

(58) Field of Classification Search
CPC ................................ A61B 5/053; A61B 5/063
See application file for complete search history.

(56) References Cited

U.S. PATENT DOCUMENTS

| | | | | |
|---|---|---|---|---|
| 7,720,529 | B1 * | 5/2010 | Schecter | 600/513 |
| 2010/0130854 | A1 * | 5/2010 | Shachar et al. | 600/424 |

* cited by examiner

*Primary Examiner* — Theodore Stigell
*Assistant Examiner* — Natasha Patel

(57) ABSTRACT

A method and system are provided for characterizing chamber specific function. The method and system comprise collecting cardiac signals associated with asynchronous timing between first and second chambers of the heart; collecting dynamic impedance (DI) data along a chamber-specific function (CSF) vector to form a DI data set, the DI data set collected during a collection window that is temporally aligned based on a timing feature of interest (FOI); repeating the collection operations over multiple cardiac cycles (CC) to obtain an ensemble of DI data sets; and combining the ensemble of DI data sets to form a composite DI data set that is coupled to a chamber functional mechanic of interest (FMOI) associated with the first chamber and decoupled from functional mechanics associated with the second chamber; and analyzing the composite DI data set to obtain a CSF indicator associated with the chamber FMOI of the first chamber.

23 Claims, 7 Drawing Sheets

METHOD AND SYSTEM FOR CHARACTERIZING CHAMBER SPECIFIC FUNCTION

FIELD OF THE INVENTION

Embodiments of the present invention generally relate to characterizing cardiac function, and more particularly to methods and systems that utilize dynamic impedance as indicators of chamber specific functions.

BACKGROUND OF THE INVENTION

Today, pacemaker configuration is often performed by selecting a desired lead location for a specific patient (e.g., septal vs apical) and then programming the parameters of the pacemaker, such as the atrioventricular (AV) and/or interventricular (VV) delay, the rate responsive AV and/or VV delay and the like. Today, cardiac resynchronization therapy (CRT) configuration is similarly performed by selecting a desired lead location (e.g., by avoiding infarct zones, reduced dyssynchrony, left ventricle (LV) apical vs septal) and then programming the CRT device with desired AV and VV delays. The AV and VV delays are selected traditionally by physicians through the use of an echocardiography evaluation method. However, the echocardiography evaluation method is time consuming and has high variations.

In addition, device manufacturers have implemented algorithms within implanted medical devices that select AV and VV delays based on intra-cardiac electrograms (IEGM). For example, one device-based method uses P-wave duration to estimate intra-atrial conduction time for setting the timing of ventricular (V) pacing. This device-based method is intended to achieve similar effects as an echocardiography evaluation based method, namely to improve atrial-filling behavior. However, device-based methods that utilize the P-wave, as detected in the right atrium (RA), represent a rough estimation of intra-atrial conduction (IACT). As such, the potential exists that the P-wave estimate may be an inaccurate estimate of IACT.

Thus, these conventional selection methods currently utilize timing features (conduction delay, dyssynchrony measures), systemic hemodynamic measures (stroke volume, pre-load) and echocardiography evaluation bases measures of cardiac function for determining ejection time, myocardial performance index, left ventricular end systole volume, and left ventricular end diastole volume.

However, it is preferred to tailor each device to the individual patient's underlying etiology and functional status. Yet, a comprehensive echocardiography evaluation assessment is time consuming. Also, when the parameters of a pacemaker are set to a preferred setting, while a patient is in the clinic, the same parameter settings may not reflect the best parameter settings for the patient when the person is ambulatory and active.

A need remains for improved methods and systems for identifying and facilitating cardiac functions such as mechanical functions of select chambers.

SUMMARY

A method and system are provided for characterizing chamber specific function. The method and system comprise collecting cardiac signals associated with asynchronous timing between first and second chambers of the heart, and collecting dynamic impedance (DI) data along a chamber-specific function (CSF) vector to form a DI data set. The DI data set is collected during a collection window that is temporally aligned with a timing feature of interest (FOI). The method and system repeat the collection operations over multiple cardiac cycles (CC) to obtain an ensemble of DI data sets. The method and system then combine the ensemble of DI data sets to form a composite DI data set that is coupled to a chamber functional mechanic of interest (FMOI) associated with the first chamber and decoupled from functional mechanics associated with the second chamber. The method and system then analyze the composite DI data set to obtain a CSF indicator associated with the chamber FMOI of the first chamber.

Optionally, the method and system may identify, from the cardiac signals, the timing FOI associated with the first chamber of the heart, wherein the timing FOI occurs asynchronously with respect to the functional mechanics of the second chamber.

Optionally, the composite DI data set may be decoupled from the functional mechanics of the second chamber such that the functional mechanics of the second chamber do not affect a morphology of the composite DI data set. Optionally, the first chamber may represent the right atrium and the chamber FMOI may represent at least one of atrial filling, atrial emptying, or atrial contractility. The analysis may comprise analyzing at least one morphologic feature of the composite DI data set, based on a CSF-DI correlation metric, to obtain the CSF indicator associated with the chamber FMOI.

Optionally, the method and system may adjust an IMD therapy configuration based on at least one CSF indicators such that the IMD operates to encourage a select level for the chamber-specific function. Optionally, the CSF-DI correlation metric represents at least one of i) a peak to peak (P-P) amplitude, ii) a minimum amplitude, iii) a minimum DI change per unit time (dZ/dt), iv) a slope, v) a select chamber filling time, or vi) a select chamber emptying time of the composite DI data.

Optionally, the method and system may determine a select level for at least one IMD therapy parameter that provides at least one of i) a select peak to peak amplitude, ii) a select minimum amplitude, iii) a select DI change per unit time (dZ/dt), iv) a select slope, v) a select chamber filling time, or vi) a select chamber emptying time, of the composite DI data when plotted over time. Optionally, the DI data collection may include utilizing an IMD case electrode and at least one of an SVC electrode and an RA electrode to define the CSF vector and to collect the DI data. Optionally, the analysis may include determining, as a morphologic feature, at least one of i) a peak to peak (P-P) amplitude, ii) a minimum amplitude, iii) a minimum DI change per unit time (dZ/dt), iv) slope, v) a select chamber filling time, or vi) a select chamber emptying time, of the composite DI data. Optionally, the method may further comprise, over sets of the cardiac cycles, modulating at least one IMD therapy parameter and repeating the collecting operations to obtain a collection of the CSF indicators.

DETAILED DESCRIPTION

Figure 1A:
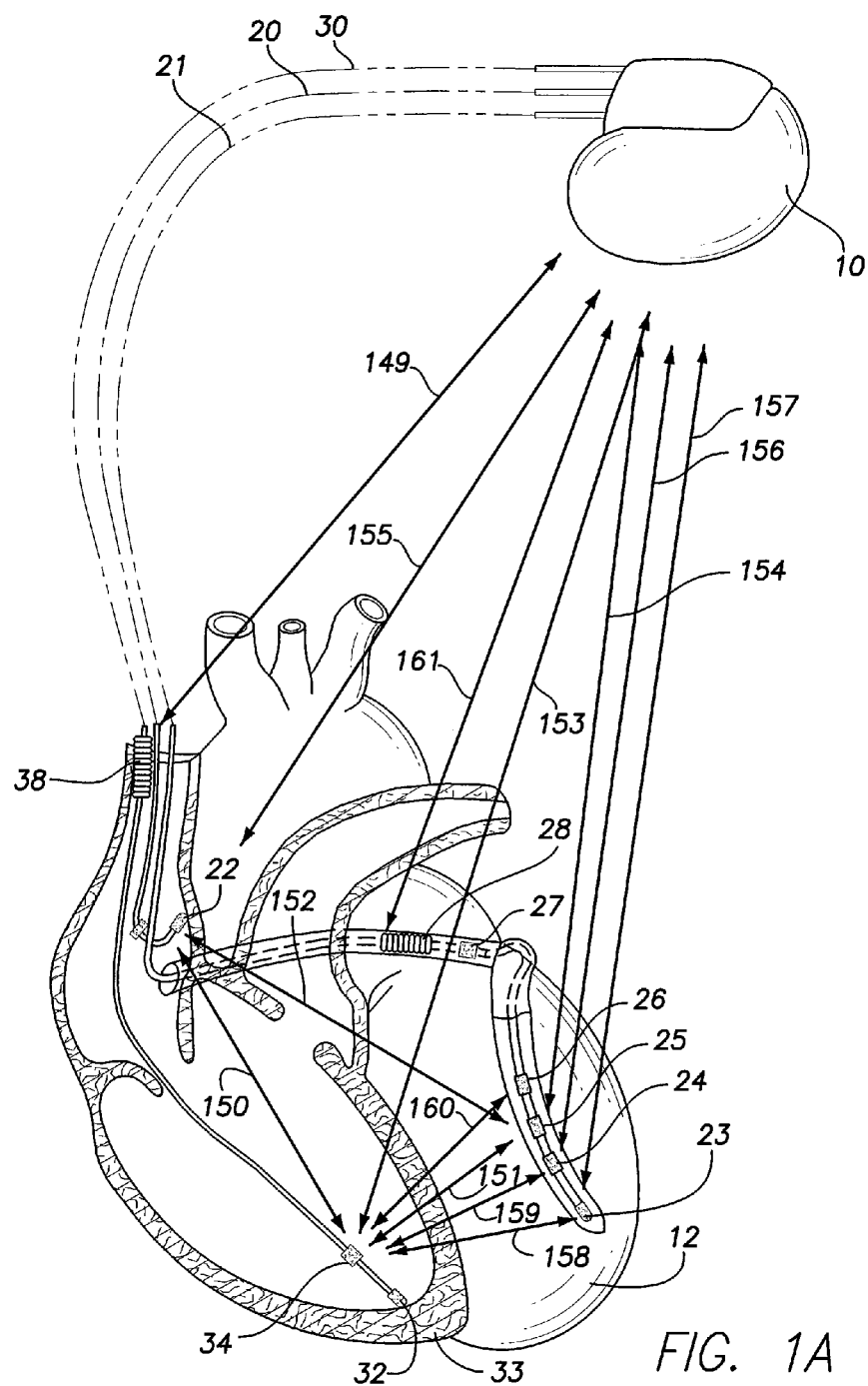
FIG. 1A illustrates a simplified diagram of an implantable medical device in electrical communication with leads implanted in or proximate to a patient's heart in accordance with an embodiment.

In accordance with embodiments herein, methods and systems are described to characterize the systemic and cardiac function of a patient on a beat-by-beat basis. A series of studies in canines were conducted to characterize the effect of hemodynamics on dynamic impedance as recorded from various anode cathode electrode combinations (using transvenous implanted leads). An analysis of the canine data has helped to provide a means of better identifying correlation between, or ways to associate specific changes in morphology of, dynamic impedance and chamber mechanical function (e.g., filling, emptying, timing). Embodiments herein are described for characterizing cardiac functions, such as venous return.

Embodiments are also described for setting parameters to improve venous return depending on a patient's specific need. For example, embodiments utilize dynamic impedance (DI) data collected along one or more vectors associated with certain cardiac chamber specific functions (CSF). For example, a CSF vector may be defined by delivering current between a superior vena cava (SVC) coil electrode and a case electrode, while measuring a voltage potential between the same or a different SVC-coil electrode and the case electrode. Optionally, a vector may be defined by delivering current (and measuring voltage potential) between a right ventricle (RV) tip, coil or ring electrode and an implantable medical device (IMD) case electrode. Specific morphological metrics (e.g., i) a peak to peak (P-P) amplitude, ii) a minimum amplitude, iii) a minimum DI change per unit time (dZ/dt), iv) a slope, v) a select chamber filling time, or vi) a select chamber emptying time) may be associated with DI data collected along the CSF vector, where the morphological metrics enable the DI data to be used to characterize a status of the patient's chamber specific function.

In general, each chamber has unique traits. Although the chambers coordinate activities to deliver blood throughout the body, each chamber exhibits specific behavioral features that aid in proper operation. For example, the tricuspid valve (TCV) regulates blood flow between the RA and the RV and thus affects proper filling and emptying of the RV and the RA. Similarly, the opening and closing of the mitral valve (MO and MC, respectively) regulates blood flow between the left atrium (LA) and the left ventricle (LV). It may be of interest to monitor the operation of each chamber for a given patient. For example, it may be of interest to monitor the filling of the RV in connection with controlling the AV and/or VV timing of an IMD.

Embodiments herein are described in which a CSF related dynamic impedance vector (SVC coil-case) is used to track a chamber specific activity on a continual basis. Based on the underlying reason for a change in a CSF, the IMD programming may be changed (manually or automatically) such that the IMD facilitates a select level of hemodynamic support. For example, the DI data recorded from a CSF vector may be used to determine chamber specific functions using one or more morphology characteristics from the DI data.

FIG. 1A illustrates a simplified diagram of an IMD 10 in electrical communication with three leads 20, 21 and 30 implanted in or proximate to a patient's heart 12 for delivering single or multi-chamber stimulation (e.g. pacing, antitachycardia pacing (ATP) therapy, high voltage shocks and the like) and for characterizing cardiac function according to an embodiment. The stimulation may include pacing pulses that are delivered along one or more pacing vectors. Optionally, the stimulation may include ATP pulses or a high voltage shock that is delivered along one or more ATP therapy vectors, cardioverter vectors or defibrillation vectors. The IMD 10 may be a pacing device, a pacing apparatus, a cardiac rhythm management device, an implantable cardiac stimulation device, an implantable cardioverter/defibrillator (ICD), a cardiac resynchronization therapy (CRT) device, a monitoring device and the like. The IMD 10 is programmable, by an operator, to set certain operating parameters, as well as therapy-related parameters. The IMD 10 is configured to operate with various configurations of leads. The IMD 10 is configured to sense various types of information and deliver various types of therapies. For example, the IMD 10 senses intracardiac electrogram signals, impedances and the like.

In FIG. 1A, the IMD 10 is coupled to an RA lead 20 having at least an atrial tip electrode 22, which typically is implanted in the patient's right atrial appendage. The IMD 10 is coupled to an LV lead 21 that includes various electrodes, such as an LV tip electrode 23, intermediate LV electrodes 24-26, and LA electrodes 27-28. The LV lead 21 may sense atrial and ventricular cardiac signals and impedances and deliver left ventricular therapy using the LV tip electrode 23, the intermediate LV electrodes 24-26, and the LA electrodes 27 and 28. Left atrial therapy uses, for example, first and second LA electrodes 27 and 28. The LV and LA electrodes 23-28 may be used as sensing sites, where cardiac signals and/or impedances are sensed, and/or may be used as pacing and/or shock therapy sites. A right ventricular lead 30 may include one or more of an RV tip electrode 32, an RV ring electrode 34, and a superior vena cava (SVC) coil electrode 38 (also known as a RA coil electrode). The right ventricular lead 30 is capable of sensing cardiac signals and/or impedances, and delivering stimulation in the form of pacing and shock therapy to the SVC and/or right ventricle.

Optionally, more or fewer electrodes may be utilized. The LV electrodes may be separated further apart or positioned closer to one another. Optionally, all or a portion of the LV electrodes may be shifted along the LV lead 21 until positioned proximate to the mitral valve, aortic valve, or the left atrial ports to/from the pulmonary veins. The LV lead 21 may be inserted directed into the LV chamber or inserted into a vein or artery extending along the heart wall proximate to the left ventricle. Optionally, the LV lead 21 may be coupled to a patch or mesh net electrode that is secured to or located adjacent to an exterior wall of the left ventricle and/or the left atrium.

Embodiments are described herein, whereby multiple electrodes are utilized to sense impedance along multiple sensing vectors in order to measure local impedance information along the select sensing vectors. Impedance measurements collected along the select sensing vectors are utilized to derive dynamic impedance data correlated to one or more cardiac functions.

The IMD 10 defines sensing vectors between various combinations of two or more electrodes 22-28, 32, 34 and 38, and the housing of the IMD 10. FIG. 1A illustrates examples of sensing vectors 149-161. The IMD 10 obtains one or more impedance measurements along the select one or more sensing vectors 149-161 which extend through a substantial majority of the portion of the heart and/or greater vessels of interest. An individual measured impedance represents the impedance of the walls of the heart 12, the blood in the heart 12 and any external tissue or muscle through which the corresponding active sensing vector extends.

The sensing vector 149 extends between the SVC coil electrode 38 and the CAN electrode of the IMD 10. The sensing vector 150 extends between the RA electrode 22 and the RV electrode 34. The sensing vector 151 extends between the RV electrode 34 and the LV electrode 25. The sensing vector 152 extends between the LV electrode 25 and the RA electrode 22. The sensing vector 153 extends between the RV electrode 34 and the CAN electrode of the IMD 10. The sensing vector 154 extends between the LV electrode 25 and the CAN electrode. The sensing vector 155 extends between the RA electrode 22 and the CAN. The sensing vector 156 extends between the LV electrode 24 and the CAN electrode. The sensing vector 157 extends between the LV electrode 23 and the CAN electrode. The sensing vector 158 extends between the RV electrode 34 and the LV electrode 23. The sensing vector 159 extends between the RV electrode 34 and the LV electrode 24. The sensing vector 160 extends between the RV electrode 34 and the LV electrode 26. The sensing vector 161 extends between the LA coil electrode 28 and the CAN electrode of the IMD 10. Optionally, alternative and/or additional electrodes may be used to form alternative and/or additional sensing vectors.

Each LV and RV electrode 22-38 represents a potential sensing site and/or therapy site. When functioning as a sensing site, the corresponding LV and/or RV electrode sense signals that are utilized to obtain cardiac signals and/or impedance measurements. The sensing sites differ based on the type of device and type of detection algorithm utilized.

For example, in a CRT-D type device, the device may utilize sensing vectors that extend between the RV electrode 34 and CAN, and between a LV ring electrode and the CAN. In an ICD type device, the device may utilize sensing vectors that extend between the RV electrode 34 and the CAN and between the RV ring electrode and the CAN. In a CRT-P type device, the device may utilize sensing vectors that extend between the LV ring electrode and the CAN, between the RA ring electrode and the CAN, and between the RV ring electrode and CAN. In a pacemaker type device, the device generally utilizes an active sensing vector that extends between the RV ring electrode and the CAN.

The impedance measured along the sensing vectors 149-161 may be expressed in terms of Ohms. Alternatively, the impedance may be expressed as an admittance measurement. The admittance may be inversely related to the impedance. The impedance measured along the sensing vectors 149-161 may vary based on a variety of factors, including the amount of fluid in one or more chambers of the heart 12 and/or thoracic space. As a result, the impedance measurement may be indicative of left atrial pressure (LAP). As more blood fills the left atrium and pulmonary veins, the LAP increases. Blood is more electrically conductive than the myocardium of the heart 12. Consequently, as the amount of blood in the left atrium increases, the LAP increases and the impedance measured along the active sensing vector decreases. Conversely, decreasing LAP may result in the impedance measurement increasing as there is less blood in the left atrium and pulmonary veins.

Optionally, impedance measurements along various sensing vectors may be utilized to monitor and characterize pressure and blood flow in other chambers of the heart, such as RA, RV, LA and/or LV pressure and blood flow.

Figure 1B:
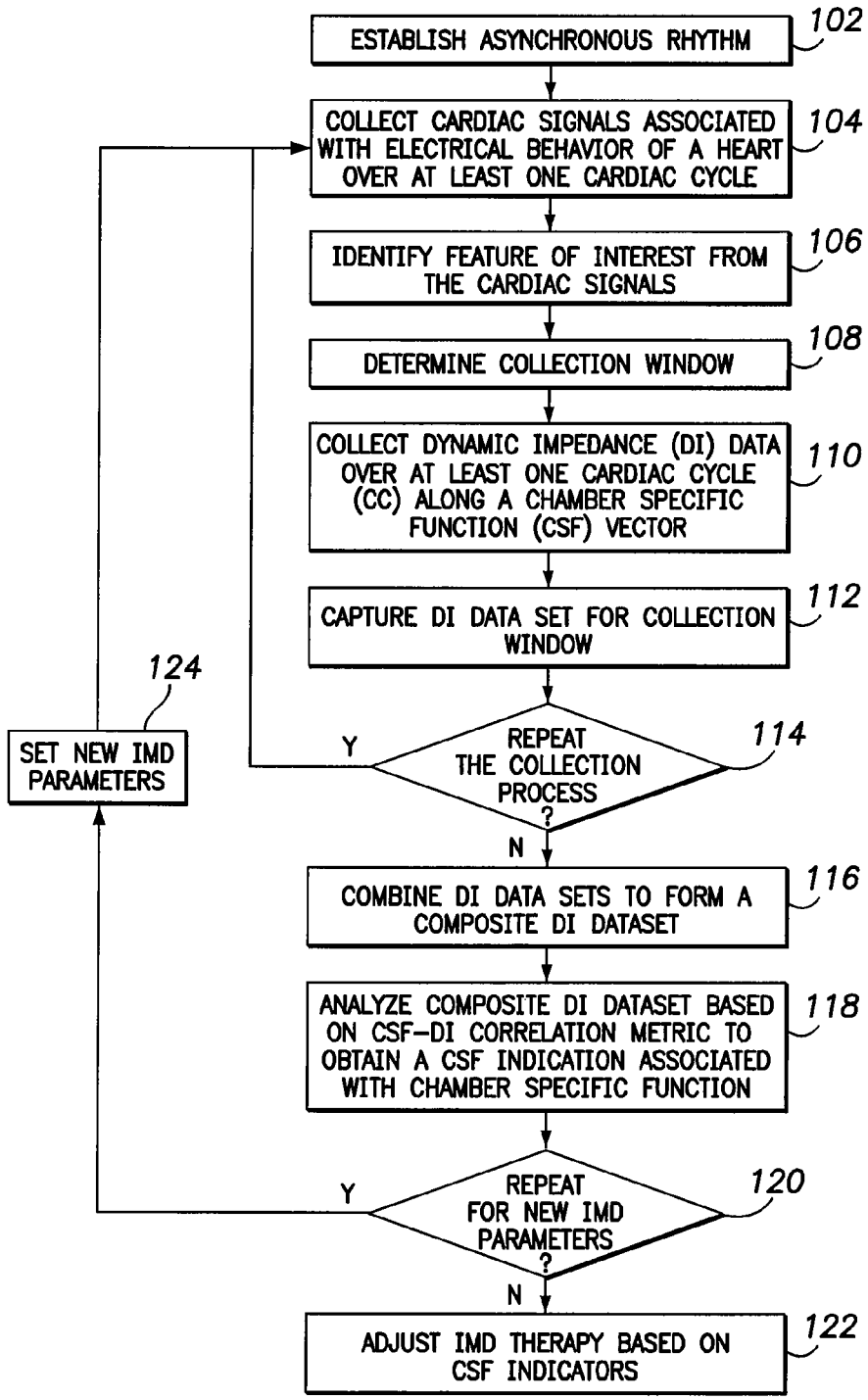
FIG. 1B illustrates a method for characterizing atrial cardiac function to be carried out in accordance with an embodiment by one or more of an IMD, external programmer and system described herein.

FIG. 1B illustrates a method for characterizing atrial cardiac function to be carried out in accordance with an embodiment by one or more of an IMD, external programmer and system described herein. The method of FIG. 1B may be carried out in connection with various chamber specific functions (CSFs). For example, the CSF may correspond to the functional mechanics of a particular chamber, such as the mechanical behavior of the mitral or tricuspid valves. The functional mechanics may correspond to atrial filling, atrial emptying and the like. The method of FIG. 1B begins with the therapy parameters of the IMD 10 set to predetermined values, based on conventional programming techniques. The IMD therapy parameters may include one or more of AV delay, VV delay, pacing electrode combination, stimulus pulse width, strength, interval and the like.

Beginning at 102, the method establishes IMD therapy parameters that encourage or facilitate asynchronous timing between at least a first and a second chamber of the heart. Asynchronous timing between chambers of the heart may be established by pacing in one chamber of the heart at a rate that is not synchronized with other chambers of the heart. An example of asynchronous timing may be the timing difference between the contraction of the right atrium and the contraction of the right ventricle. Optionally, asynchronous timing could be established between the right atrium and the left atrium. As another option, asynchronous timing could be established between the right atrium and the left ventricle. As yet another option, asynchronous timing could be established between the left atrium and the left ventricle. Optionally, asynchronous timing could be established between the right ventricle and the left ventricle. For example, the IMD 10 may pace the right ventricle at a rate of 60 beats per minute (bpm) without pacing in the right atrium, while the RA operates at an intrinsic (non-paced) rate greater than 60 bpm. As another example, the IMD 10 may pace the RA at a rate of 100 bpm, while the RV operates at an intrinsic rate below 100 bpm. Optionally, the IMD 10 may vary the pacing rate, such as between 60, 70, 80, 60, 70, 80 bpm for the RA or RV. As a further example, the IMD 10 may pace both the RA and RV (but at different rates), or both the LA and LV (but at different rates), or all four chambers but with the atria at one rate and the ventricles at a different rate to maintain asynchronous timing.

It is to be understood that asynchronous timing may include a percentage of cardiac cycles that may exhibit some degree of synchronous behavior between the atrium and the ventricle. The amount of synchronous behavior may depend on the extent the ventricle is overdriven (e.g., paced at a rate greater than the intrinsic rate). When the ventricle is overdriven at a relatively high rate, few or none of the intrinsic atrial events (e.g., events that are not paced) may cross the AV node and induce activity in the ventricle. Alternatively, when the ventricle is overdriven at a relatively lower rate, the potential may exist that an intrinsic atrial event may cross the AV node and begin activation of the ventricle, in which case, the particular beat may be synchronous. Such synchronous beats may be reduced by overdriving the ventricle at a rate greater than the intrinsic AV delay. Alternatively, such synchronous beats may be identified and filtered (e.g., removed) from the data set.

At 104, the method collects cardiac signals associated with electrical behavior of the heart while the heart exhibits asynchronous timing between the first and second chambers. The cardiac signals are collected over at least one cardiac cycle (CC) while the IMD 10 operates based on current IMD therapy parameter values. For example, the cardiac signals may be intra-cardiac electrogram (IEGM) signals, electrocardiogram (ECG) signals, and the like. The cardiac signals may be collected from external skin electrodes, the implanted electrodes 22-38 (along one or more of sensing vectors 149-161) and the like.

At 106, the method identifies a timing feature of interest (FOI) from the cardiac signals. For example, the timing feature of interest may be the peak of the R-wave, the start, the center, and/or duration of the P-wave, the ST segment, and the like. The timing feature may be intrinsic (e.g., a naturally occurring cardiac event) or paced (e.g., a paced R-wave, a paced P-wave, etc.).

The timing FOI is chosen in connection with a functional mechanic of interest (FMOI) of the heart. The FMOI of the heart may include various mechanical operations that are observable during a CC. For example, the FMOI may represent one of the filling of the RA, the opening of the TCV, the emptying of the RA, the filling of the RV, the closure of the TCV and the like. As another example, the FMOI may represent the filling of the LA, opening of the MV, emptying of the LA, filling of the LV, or closure of the MV.

Optionally, a signal may be obtained that is indicative of patient state (e.g., from an accelerometer), such as the amount of movement (indicative of exercise), the orientation of the patient with respect to gravity (prone, supine, standing, etc.) and the like. Alternatively, the cardiac signal may include information indicative of patient state. The patient state may be analyzed in order to determine when an exertion level or patient orientation is outside of a desirable correlation range. When the patient is undergoing heavy excursion, the DI data may not substantially track certain cardiac functions as closely as desired. Hence, the patient state may be used to determine whether to perform subsequent DI data collection and analysis. For example, when the patient state indicates that the patient is experiencing an excessively high heart rate, the method may determine that impedance measurements will not correlate well to the CSF of interest. Hence, flow may return to 102 and/or the method may determine to cease operation for a period of time or a predetermined number of cardiac cycles. Alternatively, when the patient state indicates that the DI data should correlate to the CSF of interest, then the flow moves to 108.

At 108, the method utilizes the timing FOI to determine a collection window. A collection window represents a period of time at which to capture data relative to a timing FOI. For example, the collection window may start a predetermined time before the start or center of a P-wave (when the P-wave represents the timing FOI). Optionally, the collection window may start a predetermined time before the start or center of an R-wave (when the R-wave represents the timing FOI). The collection window may have a predetermined duration as measured from the start time, or may end at a set time after the timing FOI and the like.

Figure 3:
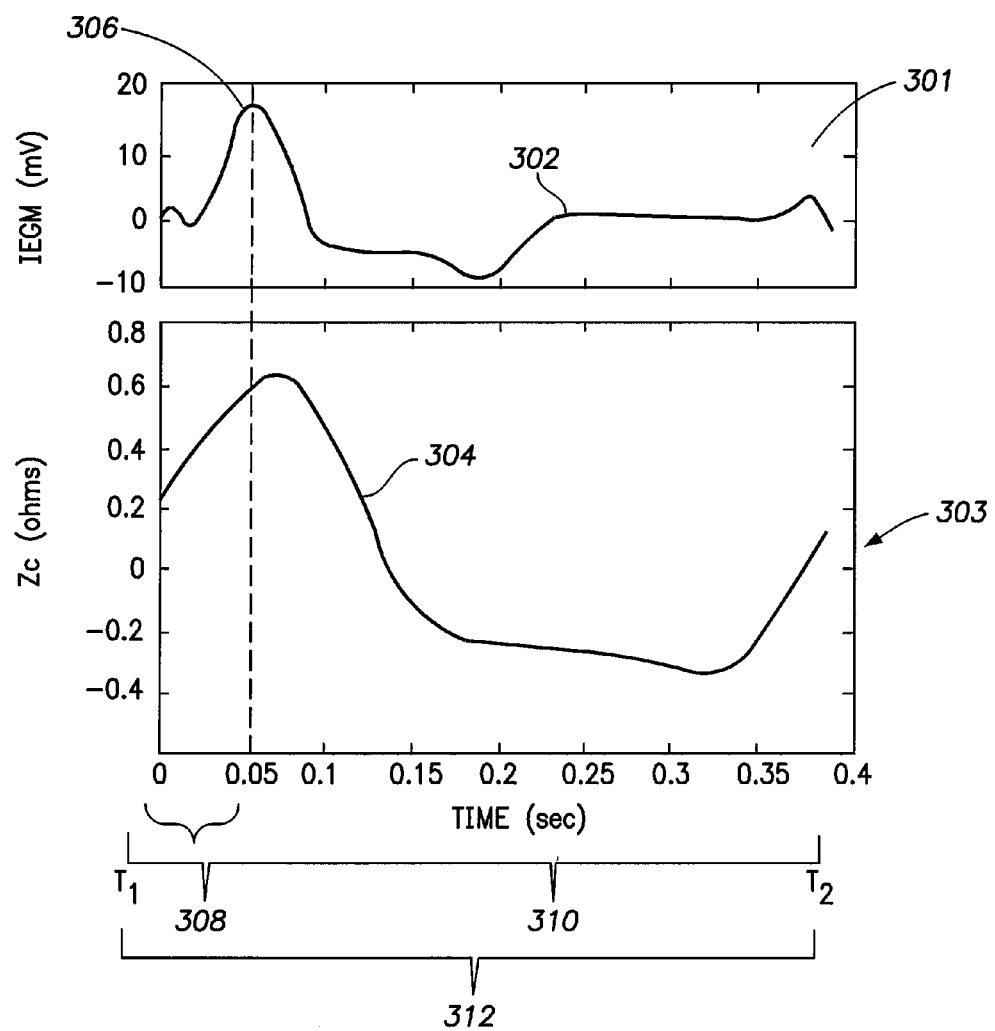
FIG. 3 illustrates examples of a cardiac signal and a DI data set relative to a collection window in accordance with an embodiment.

FIG. 3 illustrates examples of a cardiac signal 302 and a DI data set 304 relative to a collection window 312 in accordance with an embodiment. The graph 301 plots a cardiac signal 302 (e.g., an ECG signal or an IEGM signal) in millivolts along the y-axis, and time in milliseconds along the x-axis. The graph 303 plots a DI data set 304 in terms of Ohms along the y-axis, and time in seconds along the x-axis. The method of FIG. 1B continuously records a stream of cardiac signals and a stream of DI data and saves at least the stream of DI data in memory of the IMD, external programmer and the like. For example, the stream of DI data may be continuously stored in a DI buffer such that, when the DI buffer is full, the oldest DI data is written over with new DI data. As one example, the buffer may store a continuous stream of DI data for 5, 10, 20, 40, or more cardiac cycles.

The method of FIG. 1B analyzes segments of the cardiac signal 302, at 106, to identify a timing FOI 306 associated with a current cardiac cycle. For example, when the cardiac signal 302 represents an atrial IEGM signal, the timing FOI 306 may be the peak, start or center of the P-wave. For example, when the cardiac signal 302 represents a ventricular IEGM signal, the timing FOI may be the peak, start or center of the R-wave. Optionally, the timing FOI 306 may represent a predetermined paced event (e.g. when the V pace marker triggers). In the example of FIG. 3, the cardiac signal 302 represents an atrial IEGM signal and the timing FOI represents the P-wave peak.

Once the timing FOI 306 is identified, the method of FIG. 1B determines (at 108) the collection window 312. To define the start time T1 and end time T2 of the collection window 312, the method applies a window start offset 308 and a window end offset 310. The window start offset 308 extends backward in time from the timing FOI 306 to identify a point in time preceding the timing FOI 306 from which the DI data set is of interest. For example, the window start offset 308 may be 0.05 seconds, when dynamic impedance data of interest precedes the peak of the P-wave by up to 0.05 seconds. The window start offset 308 may be adjusted based upon the amount of time/data of interest to establish a DI data trend that precedes the timing FOI 306.

The window end offset 310 represents the amount of time following the timing FOI 306 until the end of the collection window 312. The window end offset 310 represents the amount of time following the timing FOI 306 that is selected to afford sufficient time to collect a sufficient amount of dynamic impedance data to characterize a chamber specific function of interest. For example, the window end offset 310 may be 0.35 seconds in length, when it is determined that dynamic impedance data of interest follows the peak of the P-wave by up to 0.35 seconds. The window end offset 310 may be adjusted based upon the amount of time/data of interest to establish a DI data trend that follows the timing FOI 306.

Optionally, the end time T2 of the collection window 312 may be defined based on an overall length of time from the start time T1. The start, end, and duration of the collection window 312 may be based on one or more of i) preprogrammed time segments, ii) time segments that are automatically calculated based on the heart rate of therapy parameters and the like. Optionally, the end time T2 may be determined based upon a second FOI, such as a peak or center of the T-wave, and the like.

At 110, the method collects a stream of DI data associated with the CSF vector while the heart exhibits asynchronous timing between the first and second chambers. The DI data stream is collected over at least one cardiac cycle (CC) while the IMD 10 operates based on current IMD therapy parameter values. For example, the DI data stream may be collected along one or more of sensing vectors 149-161, as discussed herein.

Current flux density at the surface of the sensing electrode(s) (e.g., SVC or IVC electrode or RA electrode) is relatively high as compared to the current flux density remote from the sensing electrode(s) (e.g., at other chambers of the heart or outside of the heart or at the case electrode). Due to the substantially larger current flux density immediately adjacent the sensing electrode(s), the DI data is primarily affected by changes in the impedance in the area (e.g., the blood) immediately surrounding the sensing electrode(s), while changes in the impedance in areas more remote from the sensing electrode(s) have less relative impact on changes in the dynamic impedance. As an example, the DI data may be recorded from an anode-cathode combination that delivers a reference current between an SVC coil electrode and a case electrode, while measuring voltage between the same or different SVC coil and case electrodes. Hence, when one sensing electrode is in or near the SVC, RA, LA or IVC, the CSF vector detects a DI data stream, a component which is primarily affected by changes in impedance in the proximal area surrounding the sensing electrode. When the case of the IMD is used as the second sensing electrode, this second sensing electrode is not affected by changes in impedance in the RV or LV.

Figure 2:
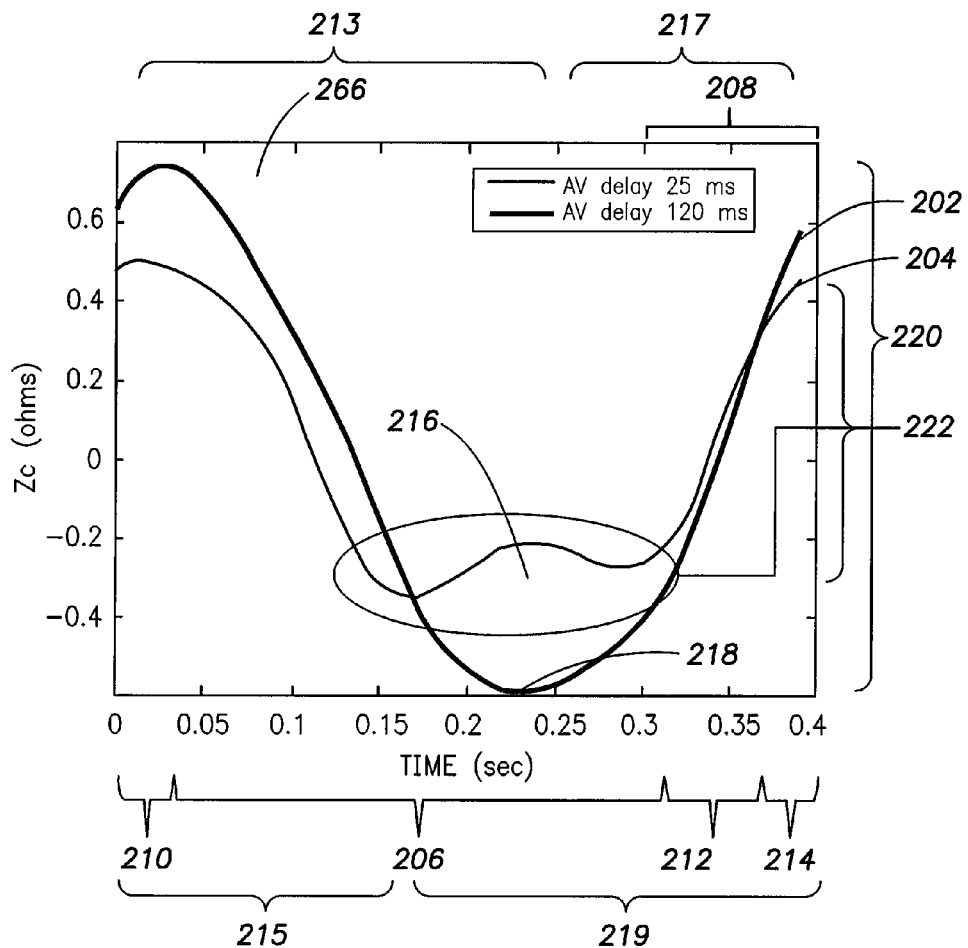
FIG. 2 illustrates a graph plotting examples of DI morphologies for patients having different stroke volumes in accordance with an embodiment.

FIG. 2 illustrates a graph 266 plotting examples of DI morphologies 202 and 204 for patients having different stroke volumes. The graph 266 plots dynamic impedance in Ohms along the y-axis, and time in seconds along the x-axis. The y-axis includes a zero level and extends ±1 Ohm. It should be recognized that FIG. 2 is an example of the dynamic component of the measured impedance. The impedance measurement will also have a DC component that is subtracted from the graph 266. The DI data has been normalized after subtracting the DC bias component such that the resultant or filtered DI data varies between +1 and −1. Hence, the graph 266 shows the DI data after the DC component is subtracted and the DI data is normalized.

In graph 266, the x-axis extends over a 400 millisecond period representing one cardiac cycle. The 0 ms point represents the V pace marker and is used to form the start of the DI data collection window. Certain cardiac time zones of interest are identified along the x-axis. The cardiac cycle includes an atrial diastole period 206 and ventricular diastole period (collectively represented by 208 and 210). The portion of the ventricular diastole period at 212 represents a passive filling zone. The portion represented by the diastole period at 214 represents an active filling one.

The DI morphologies 202 and 204 are used to characterize atrial function by applying one or more CSF-DI correlation metrics to the DI data. The DI morphology 202 represents DI data collected while the IMD therapy parameters were set with an AV delay of 120 milliseconds. The DI morphology 204 represents DI data collected while the IMD therapy parameters were set with an AV delay of 25 milliseconds. The DI morphology 204 corresponds to a suboptimal AV delay resulting in suboptimal filling of the RA, and reduced stroke volume relative to desired filling behavior and stroke volume. The malformed portion of the impedance waveform at the trough 216 indicates a reduced blood volume during part of the atrial diastole period 206. Conversely, the DI morphology 202 exhibits a greater (negative) amplitude 218, which corresponds to a desired (e.g., optimal) AV delay resulting in a select (e.g., maximized) level of stroke volume.

During systole, blood accumulates in the SVC and right atrium. As the blood accumulates, the additional blood increases the dimensions of the SVC and right atrium. As the blood from venous return accumulates in the SVC and right atrium, the impedance sensed along a CSF vector decreases because the CSF vector extends through more liquid and less tissue. Blood is more conductive than tissue, which lowers the impedance between the electrodes that define the CSF vector as the amount of blood in the IVC and SVC increases.

During ventricular diastole, the blood drains from the vena cava and the right atrium into the right ventricle. As the blood drains from the vena cava through the RA to the RV, the volume of blood in the venous region along the CSF vector decreases, thereby causing the impedance sensed along the CSF vector to increase.

The DI morphologies 202 and 204 have components that exhibit various characteristics of interest that are indicative of the cardiac function of interest when CSF-DI correlation metrics are applied. For example, one CSF-DI correlation metric is the peak to peak amplitude. The DI morphologies 202 and 204 have peak to peak amplitudes 220 and 222, respectively. A change in the peak to peak amplitudes 220 and 222 of the impedance signals directly correlate to stroke volume (SV). In general, it is desirable for the DI data to exhibit a larger peak to peak amplitude as this is an indication of larger atrial filling. The DI morphology 202 exhibits a large peak to peak amplitude 220 as compared to the peak to peak amplitude 222 of the DI morphologies 204.

Another CSF-DI correlation metric is the derivative, also referred to as dZ/dt, or slope of the DI morphology during the positive or up stroke of the DI data. The maximum positive value of the derivative (or maximum positive slope) of the up-stroke of the impedance signal forming the DI morphologies 202 and 204 are indicative of, and directly correlate to, the peak volume during the atrial filling process. The point in time at which the derivative reaches a maximum (or select) positive value can be marked as the point at which the RA has reached a select (e.g., largest or maximum) diastole state. Other aspects of the peak and/or derivative in the DI morphologies 202 and 204 may be measured and marked as the point at which the RA has reached a select (e.g., smallest or minimum) systole state.

Another CSF-DI correlation metric is the derivative (or slope) of the down-stroke of the impedance signal forming the DI morphologies 202 and 204 which is indicative of, and directly correlates to, the cardiac contractility strength. When the derivative or slope increases, this is indicative of an increase in contractility strength. When the derivative or slope decreases, this is an indication of a decrease in cardiac contractility strength. Similarly, when the derivative/slope of the CSF-DI morphologies 202 or 204 increases, this is an indication of an increase in cardiac contractility.

Another CSF-DI correlation metric may include the lead P-P time 213, 215 between the positive and negative peaks. The lead P-P time 213, 215 is indicative of the atrial filling time. The lead P-P time 213 is longer than the lead P-P time 215 which is indicative of corresponding long and short atrial filling times. As an example, when a desired atrial filling time corresponds to lead P-P time 213, then the lead P-P time 215 may be deemed too short for a desired atrial filling time.

Optionally, the CSF-DI correlation metric may include trailing P-P time 217 or 219, which correspond to atrial emptying time. The desired atrial emptying time may be determined (e.g., by a physician) to correspond to the trailing P-P time of 217.

Optionally, the lead and trailing P-P times 215, and 219 may indicate leakage in a valve, such as tricuspid valve regurgitation.

Optionally, the CSF-DI correlation metric may include a number of positive and/or negative peaks in the DI data set. When the number of +/− peaks is too high, the excess peaks may indicate a potential improper operation of a valve, such as improper tricuspid valve operation (e.g., regurgitation through the tricuspid valve). For example, the extra negative peak in the DI morphology 204 may indicate tricuspid valve regurgitation.

Returning to FIG. 1B, at 112 the method accesses the DI buffer that recorded the continuous DI data stream. At 112, the method collects a portion of the DI data stream from the DI buffer that corresponds to, and was recorded during, the collection window 312. The portion of the DI data stream corresponding to the collection window 312 represents a DI data set associated with a corresponding cardiac cycle. The DI data set was recorded over at least a portion of one CC and along at least one vector of interest, such as a chamber specific function (CSF) vector. The CSF vector is aligned such that changes in the DI data set are caused by changes in a FM of interest related to a specific chamber. For example, the CSF vector may extend through at least one of the SVC, RA, LA or IVC where a component of DI data is a function of the MC or MO. As another example, the CSF vector may be aligned such that a component of the DI data captures impedance changes due to at least one of, atrial filling, atrial emptying, and/or atrial contractility.

At 114, the method determines whether to repeat operations at 104-112. For example, it may be desirable to collect 10-20 DI data sets over 10-20 associated cardiac cycles. In this example, at 114, the method repeats the operations at 104 to 112 for the desired 10-20 times. The 10-20 DI data sets may be collected for consecutive cardiac cycles or during cardiac cycles separated over time. For example, at 114, it may be determined whether the timing between the first and second chambers remains asynchronous. The operations at 104-112 may not be repeated, or may be suspended, while the first and second chambers operate synchronously. Once the desired ensemble or number of DI data sets is collected, flow moves to 116.

At 116, the method combines a desired number or ensemble of DI data set to form a composite DI data set. As explained below in more detail in connection with FIGS. 4 and 5, the composite DI data set is coupled to a chamber FMOI associated with the first chamber and is decoupled from a chamber FMOI associated with the second chamber.

Figure 4:
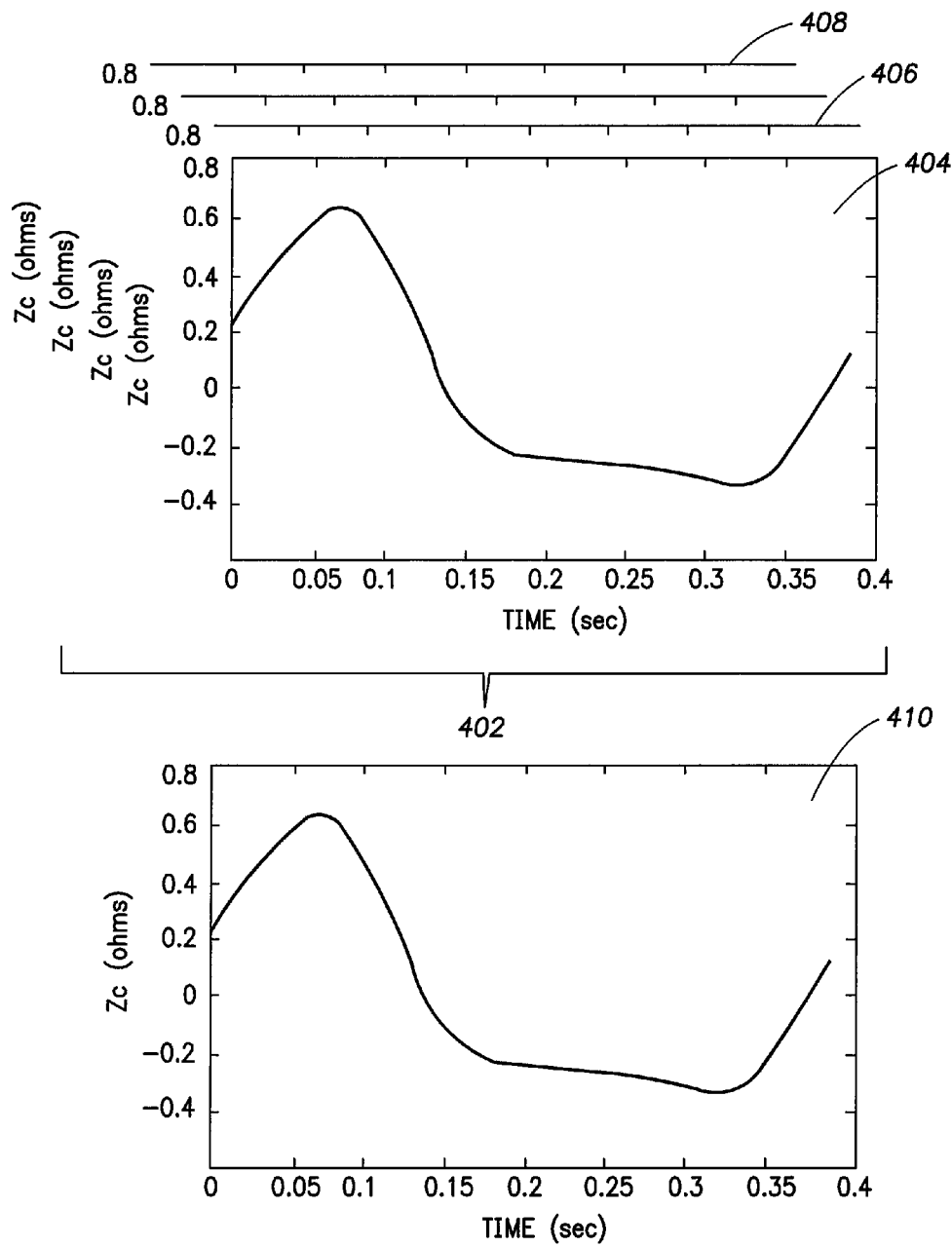
FIG. 4 illustrates a group or ensemble of DI data sets that are combined to form a composite DI data set in accordance with an embodiment.

FIG. 4 illustrates a group or ensemble 402 of DI data sets 404-408 that are combined to form a composite DI data set 410 in accordance with an embodiment. During each of the iterations through the operations at 104-112, a new DI data set 404-408 is collected and saved. For example, the DI data set 404 may correspond to a current recent cardiac cycle, while the DI data sets 406-408 correspond to immediately preceding cardiac cycles. Optionally, the DI data set 406 may correspond to a cardiac cycle that is several seconds or minutes prior to the current cardiac cycle. The y-axis represents impedance in Ohms, and the x-axis represents time in milliseconds. In the example of FIG. 4, the DI data sets are collected over a collection window of approximately 400 msec. in duration. It is understood that more or fewer DI data sets 406-408 may be saved.

In accordance with the operations at 116, the method combines the DI data sets 404-408 into a single composite DI data set 410. For example, the combining operation may represent determining an average of the DI data sets 404-408. Optionally, the combining operation may include determining a mean, median, weighted sum, correlation, variance, deviation or other statistical combination of the DI data sets 404-408. Optionally, the combining operation may utilize weighted coefficients for each DI data set 404-408. For example, more recent DI data sets may be afforded greater weight, while older DI data sets may be afforded less weight. Alternatively, the weighting may be based on a separate determination regarding a likelihood that individual DI data sets closely correlate to the CSF of interest (e.g., when the patient's state indicates the potential for close correlation). For example, when a patient is in an exercise state, the corresponding DI data sets may be afforded relatively lower weight when combined, while DI data sets collected while the patient is lying down may be afforded relatively high weight when combined into the composite DI data set 410.

When the DI data sets 404-408 are combined into the composite DI data set 410, the resulting composite DI data set 410 becomes closely coupled or correlated to functional mechanics associated with the first chamber, from which the timing FOI is derived. The resulting composite DI data set 410 is "decoupled" from or "un-correlated" with the functional mechanics of at least one other chamber.

The terms "coupled" and "correlate" are used herein to describe a link or inter-dependence between changes in at least one morphologic feature of the composite DI data set and changes in a functional mechanic of interest. For example, the functional mechanic of interest may be the operation of the tricuspid valve and the morphologic feature may represent a number of lower peaks present in the composite DI data set. The composite DI data set would be coupled or correlated to operation of the tricuspid valve where the composite DI data set exhibits one lower peak when the tricuspid valve opens and closes in a normal manner, the composite DI data set exhibits multiple (e.g., two or more) lower peaks when the tricuspid valve opens and closes in an abnormal manner (e.g., when experiencing regurgitation), As another example, the functional mechanic of interest may be atrial filling/emptying and the morphologic feature may represent a peak to peak amplitude and/or interval in the composite DI data set. The composite DI data set would be coupled or correlated to atrial filling and/or emptying operations where the composite DI data set exhibits larger peak to peak amplitude and/or interval when the right atrium fills and empties in a normal manner (e.g., time and volume), while the composite DI data set exhibits a smaller peak to peak amplitude and/or interval when the right atrium fills and empties in an abnormal manner.

The composite DI data set is coupled or correlated to atrial filling/emptying, operation of the tricuspid valve, operation of the mitral valve and the like, when changes in the composite DI data set correspond in time and magnitude with changes in atrial filling/emptying, operation of the tricuspid valve, operation of the mitral valve and the like, respectively.

The composite DI data set is similarly decoupled or un-correlated with functional mechanics of another chamber there is no link or no inter-dependence between changes in the morphologic feature of interest of the composite DI data set and changes in the functional mechanics of the other chamber. For example, when the functional mechanic of interest is the operation of the tricuspid valve and the morphologic feature is the number of lower peaks present in the composite DI data set, then the composite DI data set is decoupled or uncorrelated with the right ventricle when the mechanical functions of the RV do not affect the number of lower peaks in the composite DI data set. For example, when changes in the filling/emptying of the RV do not have any effect on the number of lower peaks in the composite DI data set, then RV filling/emptying is decoupled or un-correlated to the morphologic feature of interest. As another example, consider when the functional mechanic of interest is atrial filling/emptying and the morphologic feature is peak to peak amplitude and/or interval in the composite DI data set. The composite DI data set would be decoupled or un-correlated to RV filling and/or emptying operations when the composite DI data set exhibits random or no change in the peak to peak amplitude and/or interval when the RV fills and empties changes either in a normal or abnormal manner.

Returning to FIG. 1B, at 118, the method analyzes the composite DI data set based on at least one CSF-DI correlation metric to obtain one or more CSF indicators associated with the chamber specific function. As discussed above, the CSF-DI correlation metrics may be defined for peak to peak (P-P) amplitude, (dZ/dt) derivative of the negative portion of the DI data (dZ/dt), minimum impedance (MinZ) and the like. The CSF-DI correlation metric may optionally represent a correlation between i) the P-P amplitude, ii) the MinZ or iii) the derivative dZ/dt. The analyzing operation may include determining, as the morphologic feature, at least one of i) a peak to peak (P-P) amplitude, ii) a MinZ, iii) a dZ/dt or iv) a slope, of the average waveform data as plotted over a temporal time line for at least one CC.

Various CSF-DI correlation metrics (e.g., peak to peak amplitude and/or interval, maximum or minimum derivative in the up-stroke or down-stroke, number of minimum levels, etc.) may be used individually or in combination to monitor a functional mechanic of interest from a chamber of interest. For example, the CSF indicator(s) may represent a value or values for one or more of the peak to peak amplitude and/or interval, maximum or minimum derivative in the up-stroke or down-stroke, and/or number of minimum levels in the composite DI data set, and the like. When the CSF indicator(s) are determined, the value(s) for the CSF indicator(s) are stored in memory along with other information of interest regarding the one or more cardiac cycles associated with the composite DI data set.

Figure 5:
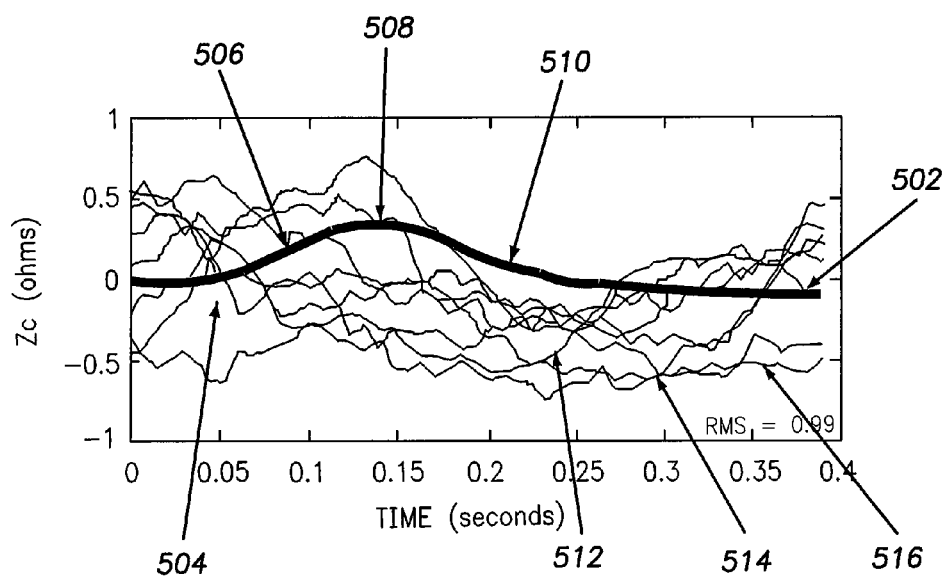
FIG. 5 illustrates a graph that exemplifies the use of a CSF-DI correlation metrics to identify chamber specific functions from a composite DI data set in accordance with an embodiment.

FIG. 5 illustrates a graph that exemplifies the use of CSF-DI correlation metrics to identify chamber specific functions from a composite DI data set. The DI morphology 502 represents composite DI data along an RV-coil vector such that the 0 ms time coincides with the peak of the P-wave. The peaks 512, 514, and 516 represent far-field noise.

One exemplary CSF-DI correlation metric that may be applied is the change in the derivative (or slope) which is indicative of, and directly correlates to the onset of the active atrial contraction period. Because blood is more conductive than tissue, the impedance between the electrodes will increase during systole. The derivative (or slope) of the DI morphology will change as the blood volume changes. By identifying the time when the derivative (or slope) changes, the onset of the active atrial contraction period can be identified. The point 504 indicates the point where the derivative changes for the DI morphology 502. Accordingly, the point 504 marks the onset of the active atrial contraction period.

Furthermore, the time between the peak of the P-wave and the onset of atrial contraction provides a measure of the electro-mechanical delay. Because the DI morphology 502 is aligned with the peak of the P-wave, the 0 ms start point coincides with the peak of the P-wave. Accordingly, the duration between time 0 and the point 504 can be used as a measure of the electro-mechanical the delay.

Another exemplary CSF-DI correlation metric is the derivative during the up stroke of the DI morphology, which provides a measure of atrial contractility. A select (e.g. maximum) value of the derivative during the up stroke of the DI morphology provides a measure of contractility. As the derivative or slope increases, this is indicative of greater contractility strength. In this example, point 506 represents the maximum positive value of the derivative for the DI morphology 502.

Yet another exemplary CSF-DI correlation metric is the peak of the DI morphology, which is indicative of and directly corresponds to the peak of atrial contraction, and the closure of the TCV. The derivative may be used to locate a peak in the DI morphology. The point at which the derivative changes from a positive value to a negative value indicates a peak in the DI morphology. Peak 508 marks the peak value for the DI morphology 502. Therefore, the peak 508 in the DI data represents the peak of atrial contraction and the closure of the TCV.

As another example, the derivative of the down-stroke of the DI morphology is indicative of, and directly correlates to, atrial compliance. A select (e.g. maximum) negative value of the derivative (or slope) results in quicker atrial recovery and greater atrial compliance. In this example, point 510 represents the maximum negative value of the derivative for the DI morphology 502.

At 120, the method determines whether the operations at 104-118 should be repeated for another group/ensemble of cardiac cycles in connection with new IMD therapy parameters. For example, at 120, it may be desirable to step through a predetermined number of IMD therapy parameter combinations (e.g., 2-5 different AV delay setting). In this example, the IMD may begin with a first set of predetermined or automatically calculated IMD therapy parameters. During the next 2-5 iterations through 104-118, the AV delay may be changed up or down by a predetermined or automatically calculated step. Once the desired number of iterations have occurred through 104-118, flow moves to 122.

Alternatively, the decision at 120 may be based on whether the CSF indicator(s) satisfy associated thresholds. For example, a physician may preprogram one or more of a threshold peak to peak amplitude and/or interval, maximum or minimum derivative in the up-stroke or down-stroke, a threshold number of minimum levels, a threshold MinZ, a threshold dZ/dt or a threshold slope, of the composite DI data set as plotted over a temporal time line. Based on the number thresholds that are satisfied, flow moves to 122 or 124.

At 124, the method changes or modulates at least one IMD therapy parameter. For example, the AV delay may be adjusted. As another example, the pacing location, pacing pulse amplitude, pacing pulse duration, pacing pulse interval and the like, may be adjusted. The AV delay or other IMD therapy parameters may be adjusted by a predetermined set amount of time, or by a variable amount of time. Optionally, the AV delay or other IMD therapy parameter may be adjusted by an amount determined automatically based on the patients past and/or current physiologic behavior.

Optionally, the modulation may include adjusting an IMD therapy configuration based on the collection of CSF-DI correlation metrics such that the IMD operates to encourage a select CSF level. Next, the flow returns to 104 and the above operations are repeated. The operations at 104-120 may be repeated a desired number of times to obtain a collection of CSF-DI metrics associated with different IMD therapy parameters.

Optionally, DI data from a CSF vector aligned through one atrium may be used to identify a timing FOI associated the other atrium. In certain patients, a sensing site may not be available in a specific atrium of interest, for example, the RA. Accordingly, the adjacent atrium may be used as a surrogate. For example, DI data sensed from a vector aligned with the LA (e.g., sensing vector 161 extending between the LA coil electrode 28 and the CAN electrode of the IMD 10) may be used in conjunction with a timing FOI in the RA. As such, the collection window 312 created at 112 may include an offset representing the mechanical activation delay between the RA and the LA. Thus, DI data sensed in the LA may be used as a surrogate to identify a timing FOI in the RA.

As another option, the operations at 104-120 may be used to determine a select (e.g., optimal) VV delay. The VV delay may be selected to encourage a ventricular function, for example, filling of the ventricle. The ventricular filling may include an active filling component resulting from the atrial kick, and a passive filling component. Generally, the atrial kick represents the amount of blood flow forced into the ventricles due to the contraction of the atria, which may be as much as 20% of the blood flow. The remaining 80% of the blood flow may be attributed to the passive filling component. As such, it may be desirable to isolate the effects of the atrial kick.

As one option, the effects of the atrial kick may be isolated or reduced (e.g., minimized) in the composite DI data by creating ensembles with varying AV and VV delays. Generally, changes in the AV delay may directly correlate to changes the amount of atrial kick. Similarly, changes in the VV delay may directly correlate to changes in passive filling. As such, the operations at 104-120 may be used to create a first ensemble containing DI data sets having a first VV delay with varying AV delays. For example, in the first ensemble, the first VV delay may be fixed at 80 milliseconds, while the AV delay is varied from 80 milliseconds to 160 milliseconds through each iteration of operations at 104-114. The operations at 104-114 may then be repeated to create a second ensemble of DI data having a second VV delay with varying AV delays. For example, the second VV delay in the second ensemble may be fixed at 90 milliseconds, while the AV delay is varied from 80 milliseconds to 160 milliseconds through each iteration of operations at 104-114. After a desired number of ensembles containing DI data based on various VV and AV delays are created, the method may combine the ensembles to create a composite DI data set as described above in the discussion regarding the operations at 116. For example, the ensembles may be averaged such that the effects of the atrial kick may be substantially reduced (e.g., minimized). The combined data set may then be analyzed at 118 using any of the CSF-DI correlation metrics described above. For example, the peak to peak amplitude of the DI morphology may be used to estimate ventricular filling.

Once the operations at 104-120 are performed a desired number of times, flow jumps to 122. At 122, the method identifies the new IMD therapy configuration that yields desired cardiac function, as indicated by the composite DI data sets and CSF indicators. For example, the method may select the CSF indicator(s) that indicate a select (e.g., maximum) RA filling time, or a select (e.g., a smallest) amount of TV or MV regurgitation, or the like. At 122, the method adjusts the IMD therapy configuration to match the chosen IMD therapy parameter settings such that the IMD operates to encourage the select CSF.

Figure 6:
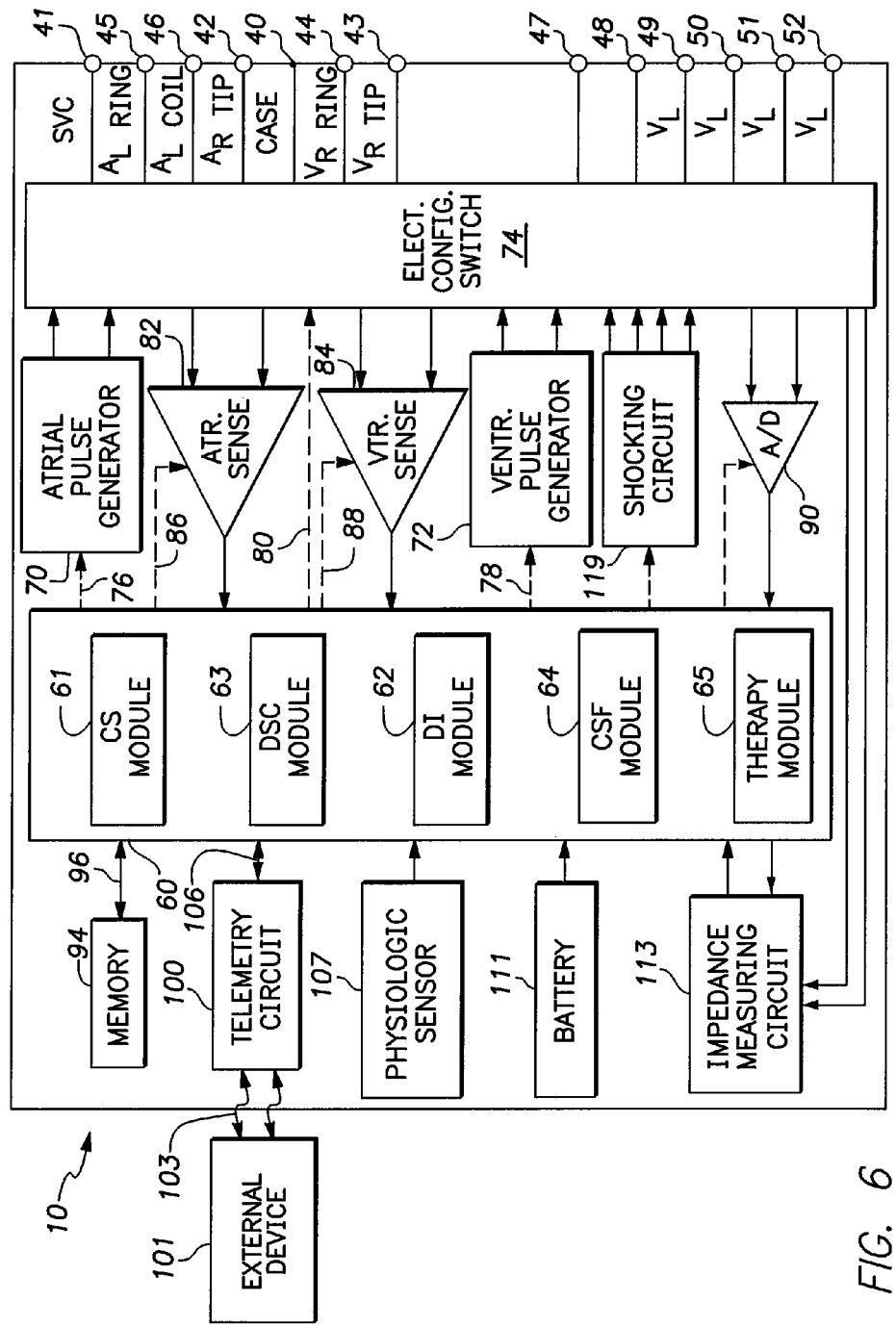
FIG. 6 illustrates a block diagram of an IMD configured to implement the methods described herein to characterize chamber specific function in accordance with an embodiment.

FIG. 6 illustrates a block diagram of the IMD 10, which is capable of performing the methods described herein and of treating one or both of fast and slow arrhythmias with stimulation therapy, including cardioversion, defibrillation, and pacing stimulation. While a particular multi-chamber device is shown, this is for illustration purposes only. It is understood that the appropriate circuitry could be duplicated, eliminated or disabled in any desired combination to provide a device capable of simply monitoring impedance and/or cardiac signals, and/or treating the appropriate chamber(s) with cardioversion, defibrillation and pacing stimulation.

The housing 40 for the stimulation IMD 10 is often referred to as the "can", "case" or "case electrode" and may be programmably selected to act as the return electrode for some or all sensing modes. The housing 40 may further be used as a return electrode alone or in combination with one or more of the electrodes of FIG. 1A for shocking purposes. The housing 40 further includes a connector (not shown) having a plurality of terminals 41-52. To achieve sensing, pacing and shocking in desired chambers of the heart, the terminals 41-52 are selectively connected to corresponding combinations of electrodes 22-38.

The IMD 10 includes a programmable microcontroller 60 that controls the various modes of sensing and stimulation therapy. The microcontroller 60 includes a microprocessor, or equivalent control circuitry, designed specifically for controlling sensing impedance derivation and the delivery of stimulation therapy and may further include RAM or ROM memory, logic and timing circuitry, state machine circuitry, and I/O circuitry. The microcontroller 60 includes the ability to process or monitor input signals (data) as controlled by a program code stored in memory. The details of the design and operation of the microcontroller 60 are not critical to the present invention. Rather, any suitable microcontroller 60 may be used.

The microcontroller 60 includes inputs that are configured to collect cardiac signals associated with electrical or mechanical behavior of a heart over at least one cardiac cycle. The cardiac signals may be IEGM signals from the atrial or ventricular sensing circuits 82 and 84 that are representative of electrical behavior of the heart. Optionally, the cardiac signals may be the output of the A/D circuit 90 that are representative of electrical behavior of the heart. The cardiac signals may be the output of the physiologic sensor 107 that are representative of mechanical behavior. As one example, the inputs are configured to collect the DI data utilizing an IMD case electrode and at least one of an SVC electrode, an IVC electrode and an RA electrode to define the CSF vector.

The microcontroller 60 includes a cardiac signal (CS) module 61, a dynamic impedance (DI) module 62, a data set compiler (DSC) module 63, a cardiac specific function (CSF) analysis module 64, and a therapy module 65 (among other things).

The CS module 61 is configured to establish an asynchronous timing between a first and a second chamber of the heart. The CS module 61 is further configured to identify a timing FOI from the cardiac signals wherein the timing FOI occurs asynchronously with respect to the functional mechanics of the second chamber.

The DI module 62 is configured to collect dynamic impedance (DI) data over at least one cardiac cycle, designated by the timing FOI, along at least one chamber specific function vector. The DI module 62 may collect DI data in collection with a select activity state and a select posture of a patient.

The data set compiler (DSC) module 63 is configured to combine the ensemble of DI data sets to form a composite data set that is coupled to a functional mechanic of interest (FMOI) of the first chamber and decoupled from the functional mechanics of the second chamber such that the functional mechanics of the second chamber do not affect a morphology of the composite data set.

The CSF analysis module 64 is configured to analyze at least one morphologic feature of the composite data set based on a CSF-DI correlation metric to obtain a CSF indicator associated with the chamber FMOI of the first chamber. The CSF-DI correlation metric may be at least one of i) a peak to peak (P-P) amplitude, ii) a minimum amplitude, iii) a minimum DI change per unit time (dZ/dt), iv) a slope, v) a select chamber filling time, or vi) a select chamber emptying time, of the composite DI data. Optionally, the morphologic feature may be at least one of i) a peak to peak (P-P) amplitude, ii) a minimum amplitude, iii) a minimum DI change per unit time (dZ/dt), iv) a slope, v) a select chamber filling time, or vi) a select chamber emptying time, of the composite DI data.

The therapy module 65 is configured to modulate, over multiple cardiac cycles, at least one therapy parameter while the IMD 10 obtains a collection of at least one CSF indicators associated with different therapy parameters. The therapy module 65 is further configured to adjust a therapy configuration based on the collection of CSF indicators and the CSF-DI correlation metric such that the system operates to encourage a select CSF level.

The memory 94 stores correlation metrics associated with the cardiac functions of interest, such as CSF-DI correlation metrics. The memory 94 also stores the CSF indicators, DI data, cardiac signals, and associated IMD therapy parameter values for each iteration through the methods of FIG. 1B.

An atrial pulse generator 70 and a ventricular pulse generator 72 generate pacing and ATP stimulation pulses for delivery by desired electrodes. The electrode configuration switch 74 (also referred to as switch bank 74) controls which terminals 41-52 receive shocks or pacing pulses. The atrial and ventricular pulse generators, 70 and 72, may include dedicated, independent pulse generators, multiplexed pulse generators, shared pulse generators or a single common pulse generator. The pulse generators 70 and 72 are controlled by the microcontroller 60 via appropriate control signals 76 and 78, respectively, to trigger or inhibit stimulation pulses. The microcontroller 60 further includes timing control circuitry which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, PVARP intervals, noise detection windows, evoked response windows, alert intervals, marker channel timing, etc.

An electrode configuration switch 74 connects the sensing electronics to the desired terminals 41-52 of corresponding sensing electrodes 22-38. For example, terminals 49-52 may be coupled to LV electrodes 23-26. The switch 74 may connect terminals 41-52 to one or more ventricular sensing circuits 84, which provide cardiac signals, representative of cardiac activity, to the microcontroller. The circuit 84 may amplify, filter, digitize and/or otherwise process the sensed cardiac signals from the LV electrodes 23-26. The circuit 84 may provide separate, combined or difference signals to the microcontroller 60 representative of the sensed signals from the LV electrodes 23-26. The circuit 84 may also receive sensed signals from RV electrodes 32 and 34 through terminals 43 and 44. The atrial sensing circuit 82 is connected through the switch 74 terminals 42 and 45-46 to desired RA and/or LA electrodes 22 and 27-28 to sense RA and/or LA cardiac activity. The switch 74 also connects various combinations of the electrodes 22-38 to an impedance measurement circuit 113.

An impedance measuring circuit 113 includes inputs to collect multiple measured impedances between corresponding multiple combinations of electrodes 22-38. For example, the impedance measuring circuit 113 may collect a measured impedance for each or a subset of the active sensing vectors 151-155. Optionally, the impedance measuring circuit 113 may also monitor lead impedance during the acute and chronic phases for proper lead positioning or dislodgement; detects operable electrodes and automatically switches to an operable pair if dislodgement occurs; measures respiration or minute ventilation; measures thoracic impedance for determining shock thresholds; detects when the device has been implanted; measures stroke volume; and detects the opening of heart valves, etc.

The switch bank 74 includes a plurality of switches for connecting the desired electrodes to the appropriate I/O circuits, thereby providing complete electrode programmability. The switch 74, in response to a control signal 80 from the microcontroller 60, determines the polarity of the stimulation pulses (e.g., unipolar, bipolar, co-bipolar, etc.) by selectively closing the appropriate combination of switches (not specifically shown). Atrial sensing circuits 82 and ventricular sensing circuits 84 may also be selectively coupled to the right atrial lead 20, LV lead 21, and the RV lead 30, through the switch 74 for detecting the presence of cardiac activity in each of the four chambers of the heart. The switch 74 determines the "sensing polarity" of the cardiac signal by selectively closing the appropriate switches.

The outputs of the atrial and ventricular sensing circuits 82 and 84 are connected to the microcontroller 60 which, in turn, is able to trigger or inhibit the atrial and ventricular pulse generators 70 and 72, respectively. The sensing circuits 82 and 84, in turn, receive control signals over signal lines 86 and 88 from the microcontroller 60 for purposes of controlling the gain, threshold, the polarization charge removal circuitry (not shown), and the timing of any blocking circuitry (not shown) coupled to the inputs of the sensing circuits, 82 and 86.

Cardiac signals are also applied to the inputs of an analog-to-digital (ND) data acquisition system 90. The data acquisition system 90 is configured to acquire intracardiac electrogram signals, convert the raw analog data into a digital signal, and store the digital signals for later processing and/or telemetric transmission to an external IMD 10. The data acquisition system 90 samples cardiac signals across any pair of desired electrodes. The data acquisition system 90 may be coupled to the microcontroller 60, or other detection circuitry, for detecting an evoked response from the heart 12 in response to an applied stimulus, thereby aiding in the detection of "capture." Capture occurs when an electrical stimulus applied to the heart is of sufficient energy to depolarize the cardiac tissue, thereby causing the heart muscle to contract.

The microcontroller 60 is further coupled to a memory 94 by a suitable data/address bus 96. The memory 94 stores programmable operating, impedance measurements, impedance derivation and therapy-related parameters used by the microcontroller 60. The operating and therapy-related parameters define, for example, pacing pulse amplitude, pulse duration, electrode polarity, rate, sensitivity, automatic features, arrhythmia detection criteria, and the amplitude, wave shape and vector of each stimulating pulse to be delivered to the patient's heart 12 within each respective tier of therapy.

The impedance derivation parameters may include information designating i) sensing electrodes to use to define active sensing vectors, ii) sets and subsets of sensing vectors to use to monitor various regions of the heart, iii) sets or subsets of active sensing vectors to combine to form each pseudo sensing vector, iv) weight valves to use with active sensing vectors to form each pseudo sensing vector, v) algorithms for how to mathematically combine active sensing vectors to form each pseudo sensing vector, and the like.

The operating and therapy-related parameters may be non-invasively programmed into the memory 94 through a telemetry circuit 100 in telemetric communication with the external IMD 10, such as a programmer, trans-telephonic transceiver, or a diagnostic system analyzer. The telemetry circuit 100 is activated by the microcontroller 60 by a control signal. The telemetry circuit 100 advantageously allows intracardiac electrograms and status information relating to the operation of the IMD 10 (as contained in the microcontroller 60 or memory 94) to be sent to an external device 101 through an established communication link 103.

The stimulation IMD 10 may include a physiologic sensor 107 to adjust pacing stimulation rate according to the exercise state of the patient. The physiological sensor 107 may further be used to detect changes in cardiac output, changes in the physiological condition of the heart, or diurnal changes in activity (e.g., detecting sleep and wake states). The battery 111 provides operating power to all of the circuits shown in FIG. 6.

The microcontroller 60 further controls a shocking circuit 117 by way of a control signal. The shocking circuit 117 generates stimulating pulses of low (up to 0.5 Joules), moderate (0.5-10 Joules), or high energy (11 to 40 Joules), as controlled by the microcontroller 60. Stimulating pulses are applied to the patient's heart 12 through at least two shocking electrodes, and as shown in this embodiment, selected from the left atrial (LA) coil electrode 28, the RV electrode 34, the SVC coil electrode 38 and/or the housing 40.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. §112, sixth paragraph, unless and until such claim limitations expressly use the phrase "means for" followed by a statement of function void of further structure.

What is claimed is:

1. A method for characterizing cardiac function, the method comprising:
    collecting cardiac signals associated with asynchronous timing between first and second chambers of the heart using one or more sensors coupled to the heart;
    collecting dynamic impedance (DI) data along a chamber-specific function (CSF) vector to form a DI data set, the DI data set collected during a collection window that is temporally aligned based on a timing feature of interest (FOI);
    repeating the collection operations over multiple cardiac cycles (CC) to obtain an ensemble of DI data sets; and
    combining the ensemble of DI data sets to form a composite DI data set that is coupled to a chamber functional mechanic of interest (FMOI) associated with the first chamber and decoupled from functional mechanics associated with the second chamber;
    analyzing the composite DI data set to obtain a CSF indicator associated with the chamber FMOI of the first chamber; and
    adjusting an IMD therapy configuration based on at least one CSF indicator to encourage a select level for the chamber-specific function.

2. The method of claim 1, further comprising identifying, from the cardiac signals, the timing FOI associated with the first chamber of the heart, wherein the timing FOI occurs asynchronously with respect to the functional mechanics of the second chamber.

3. The method of claim 1, wherein the composite DI data set is decoupled from the functional mechanics of the second chamber such that the functional mechanics of the second chamber do not affect a morphology of the composite DI data set.

4. The method of claim 1, wherein the first chamber represents the right atrium and the chamber FMOI represents at least one of atrial filling, atrial emptying or atrial contractility.

5. The method of claim 1, wherein the first chamber represents the right atrium and the chamber FMOI represents a surrogate for at least one of mitral valve closure or mitral valve opening.

6. The method of claim 1, wherein the analyzing comprises analyzing at least one morphologic feature of the composite DI data set based on a CSF-DI correlation metric to obtain the CSF indicator associated with the chamber FMOI.

7. The method of claim 6, wherein the CSF-DI correlation metric represents at least one of i) a peak to peak (P-P) amplitude, ii) a minimum amplitude, iii) a minimum DI change per unit time (dZ/dt), iv) a slope, v) a select chamber filling time, or vi) a select chamber emptying time, of the composite DI data.

8. The method of claim 1, further comprising determining a select level for at least one IMD therapy parameter that provides at least one of i) a select peak to peak amplitude, ii) a select minimum amplitude, iii) a select DI change per unit time (dZ/dt), iv) a select slope, v) a select chamber filling time, or vi) a select chamber emptying time, of the composite DI data when plotted over time.

9. The method of claim 1, wherein the collecting of DI data includes utilizing an IMD case electrode and at least one of an SVC electrode and an RA electrode to define the CSF vector and to collect the DI data.

10. The method of claim 1, wherein the analyzing includes determining, as a morphologic feature, at least one of i) a peak to peak (P-P) amplitude, ii) a minimum amplitude, iii) a minimum DI change per unit time (dZ/dt), iv) slope, v) a select chamber filling time, or vi) a select chamber emptying time, of the composite DI data.

11. The method of claim 1, further comprising, over sets of the cardiac cycles, modulating at least one IMD therapy parameter and repeating the collecting operations to obtain a collection of the CSF indicators.

12. A system for characterizing cardiac function, comprising:
    inputs configured to collect cardiac signals associated with electrical or mechanical behavior of a heart over at least one cardiac cycle (CC) while maintaining asynchronous timing between first and second chambers;
    a memory coupled to the inputs configured to store the cardiac signals;
    a microcontroller coupled to the memory and configured to control system sensing and stimulation therapy, the microcontroller comprising,
        a cardiac signal module coupled to the memory and configured to identify a timing feature of interest (FOI) from the stored cardiac signals;
        a dynamic impedance (DI) module configured to collect DI data along at least one chamber specific function (CSF) vector to form a DI data set, the DI data set collected during a collection window that is temporally aligned based on the timing FOI;

a data set compiler module configured to form a composite data set from an ensemble of DI data sets that are coupled to a chamber functional mechanic of interest (FMOI) associated with the first chamber and decoupled from functional mechanics associated with a second chamber; and a CSF analysis module configured to analyze the composite data set to obtain a CSF indicator associated with the FMOI of the first chamber.

13. The system of claim 12, wherein the cardiac signal module is configured to identify, from the cardiac signals, the timing FOI associated with the first chamber of the heart, wherein the timing FOI occurs asynchronously with respect to the functional mechanics of the second chamber.

14. The system of claim 12, wherein the composite DI data set is decoupled from the functional mechanics of the second chamber such that the functional mechanics of the second chamber do not affect a morphology of the composite DI data set.

15. The system of claim 12, wherein the first chamber represents the right atrium and the chamber FMOI represents at least one of atrial filling, atrial emptying or atrial contractility.

16. The system of claim 12, wherein the first chamber represents the right atrium and the chamber FMOI represents a surrogate for at least one of mitral valve closure or mitral valve opening.

17. The system of claim 12, wherein the CSF module is configured to analyze at least one morphologic feature of the composite DI data set based on a CSF-DI correlation metric to obtain the CSF indicator associated with the chamber FMOI.

18. The system of claim 12, further comprising a therapy module configured to adjust an IMD therapy configuration based on at least one CSF indicators such that the IMD operates to encourage a select level for the chamber-specific function.

19. The system of claim 17, wherein the CSF-DI correlation metric represents at least one of i) a peak to peak (P-P) amplitude, ii) a minimum amplitude, iii) a minimum DI change per unit time (dZ/dt), iv) a slope, v) a select chamber filling time, or vi) a select chamber emptying time, of the composite DI data.

20. The system of claim 12, further comprising determining a select level for at least one IMD therapy parameter that provides at least one of i) a select peak to peak amplitude, ii) a select minimum amplitude, iii) a select DI change per unit time (dZ/dt), iv) a select slope, v) a select chamber filling time, or vi) a select chamber emptying time, of the composite DI data when plotted over time.

21. The system of claim 12, wherein the collecting of DI data includes utilizing an IMD case electrode and at least one of an SVC electrode and an RA electrode to define the CSF vector and to collect the DI data.

22. The system of claim 12, wherein the analyzing includes determining, as a morphologic feature, at least one of i) a peak to peak (P-P) amplitude, ii) a minimum amplitude, iii) a minimum DI change per unit time (dZ/dt), iv) slope, v) a select chamber filling time, or vi) a select chamber emptying time, of the composite DI data.

23. The system of claim 12, further comprising, over sets of the cardiac cycles, modulating at least one IMD therapy parameter and repeating the collecting operations to obtain a collection of the CSF indicators.

* * * * *